(12) United States Patent
Marin et al.

(10) Patent No.: US 6,881,739 B1
(45) Date of Patent: Apr. 19, 2005

(54) USE OF CORTISOL ANTAGONISTS IN THE TREATMENT OF HEART FAILURE

(76) Inventors: Per Marin, Nolebrunnsgatan 25, Västra Frölunda (SE), S-426 77; Sten Sorensen, Västervångsvägen 22, Falstebo (SE), S-239 40

( * ) Notice: Subject to any disclaimer, the term of this patent is extended or adjusted under 35 U.S.C. 154(b) by 0 days.

(21) Appl. No.: 10/019,613

(22) PCT Filed: Jul. 3, 2000

(86) PCT No.: PCT/GB00/02551

§ 371 (c)(1),
(2), (4) Date: May 7, 2002

(87) PCT Pub. No.: WO01/01971

PCT Pub. Date: Jan. 11, 2001

(30) Foreign Application Priority Data

Jul. 2, 1999 (GB) ............................................. 9915625

(51) Int. Cl.$^7$ ........................................... A61K 31/497
(52) U.S. Cl. ................................................. 514/254.01
(58) Field of Search ............................ 514/179, 254.01

(56) References Cited

U.S. PATENT DOCUMENTS

| | | | |
|---|---|---|---|
| 4,603,141 A | | 7/1986 | Giles |
| 5,175,144 A | * | 12/1992 | Walser ........................... 514/2 |
| 5,565,478 A | * | 10/1996 | Kohn et al. .................. 514/359 |
| 5,654,293 A | | 8/1997 | Francois ...................... 514/171 |
| 5,756,469 A | * | 5/1998 | Beale ............................ 514/23 |
| 6,362,173 B1 | * | 3/2002 | Schatzberg et al. .......... 514/179 |

FOREIGN PATENT DOCUMENTS

| | | |
|---|---|---|
| HU | 212051 | 1/1996 |
| HU | 221319 | 9/2002 |
| WO | WO 9200057 | 1/1992 |
| WO | 0018424 | 4/2000 |
| WO | 0024402 | 5/2000 |

OTHER PUBLICATIONS

Faggiano P, D'Aloia A, Gualeni A, Giordano A. Hemodynamic profile of submaximal constant workload exercise i patients with heart failure secondary to ischemic or idiopathic dilated cardiomyopathy. Am J Cardiol 1998 Fe 15;81(4):437–442.

Ganiats TG, Browner DK, Dittrich HC. Comparison of Quality of Well–Being scale and NYHA functional statu classification in patients with atrial fibrillation. New York Heart Association. Am Heart J May 1998; 135(5 Pt 1):819 824.

Spitz IM, Bardin CW. Mifepristone (RU 486)—a modulator of progestin and glucocorticoid action. N Engl J Me Aug. 5, 1993; 329(6):404–412.

Scheuer DA, Mifflin SW. Chronic cortisone treatment increases myocardial infarct size in rats with ischemia reperfusion injury. Am J Physiol Jun. 1997; 272(6 Pt 2):R2017–2024.

Rotstein DM, Kertesz DJ, Walker KA, Swinney DC. Stereoisomers of ketoconazole: preparation and biologic activity. J Med Chem Jul. 24, 1992; 35(15):2818–2825.

Dvortsin GF. Use of a synthetic opioid for the reversal of stress–induced damage of the myocardium and gastr mucosa in severe thermal trauma [In Russian]. Kardiologiia Sep. 1989; 29(9):81–83.

Aggernaes H, Kirkegaard C, Magelund G. The effect of sodium valproate on serum cortisol levels in healthy subjec and depressed patients. Acta Psychiatr Scand Feb. 1988; 77(2):170–174.

Slowinska–Srzednicka J, Zgliczynski S, Soszynski P, Pucilowska J, Wierzbicki M, Jeske W. Effect of clonidine o beta–endorphin, ACTH and cortisol secretion in essential hypertension and obesity. Eur J Clin Pharmaco 1988;35(2):115–121.

Legros JJ, Chiodera P, Geenen V, von Frenckell R. Confirmation of the inhibitory influence of exogenous oxytocin o cortisol and ACTH in man: evidence of reproducibility. Acta Endocrinol (Copenh) Mar. 1987; 114(3):345–349.

Loose DS, Stover, EP, Feldman D. Ketoconazole binds to glucocorticoid receptors and exhibits glucorticoi antagonist activity in cultured cells. J. Clin Invest Jul. 1983; 72(1):404–408.

Stubbs, WA, Delitala G, Jones A, Jeffcoate WJ, Edwards CR, Ratter SJ, Besser GM, Bloom SR, Alberti KG Hormonal and metabolic responses to an enkephalin analogue in normal man. Lancet Dec. 9, 1978; 2(8102):1225–1227.

* cited by examiner

Primary Examiner—Raymond J. Henley, III
(74) Attorney, Agent, or Firm—Baker Botts LLP

(57) ABSTRACT

The present invention relates to the use of a cortisol antagonist in the manufacture of a medicament for the treatment of heart failure as well as to a method of treating heart failure which comprises administration of a cortisol antagonist and to a product containing (a) a cortisol antagonist and (b) a second drug as a combined preparation for simultaneous, separate or sequential use in the treatment of heart failure or in improving cardiac function and reducing exercise intolerance.

13 Claims, No Drawings

USE OF CORTISOL ANTAGONISTS IN THE TREATMENT OF HEART FAILURE

CROSS REFERENCES TO RELATED APPLICATIONS

This application is a national stage filing of International Patent Application PCT/GB00/02551, filed 3 Jul. 2000, which claims priority from Great Britain Patent Application 9915625.9, filed 2 Jul. 1999.

The present invention relates to heart failure and in particular to the use of a particular class of compounds for the treatment of heart failure.

Heart failure, which is generally characterised by impaired cardiac function and exercise intolerance affects a very large number of people worldwide, particularly in the Western world. Heart failure and its complications are responsible for premature death in a proportion of sufferers and generally curtails the working life and range of activities which can be undertaken by the sufferer, as well significantly reducing overall quality of life. Heart failure is found in both sexes, young and old but is particularly prevalent in males and elderly or middle aged people.

Heart failure may be caused by a number of different underlying heart diseases. Heart diseases and events which may be a factor in causing heart failure include valvular heart disease, valvular stenosis, heart muscle disease, myocardial ischemia or infarction, cardiomyopathia and infiltrative process or inflammatory process of either the muscle, endocardium or epicardium of the heart.

As heart failure is a common and serious condition, significant efforts have been made by the medical community towards developing treatments for heart failure. A successful treatment should improve quality of life, prevent or slow progression of cardiac dysfunction and prolong life. Non-pharmacological treatments include modified diets to reduce sodium retention and cause weight loss and exercise programmes, although there is a conflict between the need to improve ventricular performance which is aided by bed rest and a desire to improve exercise intolerance and maintain conditioning which is favoured by a moderate exercise regime. In some cases heart failure will be treated by surgical means including full heart transplantation.

A number of pharmaceuticals are available for the treatment of heart failure and for the most part these fall into three broad categories, diuretics, vasodilators and inotropic drugs. Diuretic therapy seeks to maintain intravascular volume at the lowest level compatible with optimal cardiac performance. A reduction in intravascular volume has the advantage of reducing interstitial fluid by allowing its reabsorption into the vascular space. Furosemide and/or metolazone have been used as diuretics in the treatment of heart failure but the use of these and other diuretics may lead to an undesirable drop in intracellular potassium levels. Potassium levels should be monitored and potassium supplementation may be required.

Vasodilator drugs may be useful in increasing stroke volume due to a reduction in vascular impedance and in reducing preload due to an increase in venous capacitance. Optimal treatment using vasodilators will often require coadministration of an arterial dilator such a hydralazine or minoxidil and a venodilator such as isosorbide dinitrate.

Treatment with a diuretic and/or vasodilator may be supplemented by an inotropic drug such as digoxin, dobutamine or aminone.

In addition, a patient suffering from heart failure may, in certain circumstances be prescribed antiarrhythmic drugs, β-adrenoreceptor blockers, anticoagulants, an angiotensin-converting enzyme (ACE) inhibitor or an angiotensin II antagonist.

While a large number of pharmaceuticals are available to the physician for treating heart failure, different patients will have different needs and successful treatment will often require administration of a range of complementary drugs. Adverse reactions by some patients to particular drugs and drug intolerance means there is a continuing demand for new drugs of use in the treatment of heart failure, as physicians strive to find the best drug or combination of drugs for each sufferer. Moreover, heart disease is so widespread that the public and doctors alike demand ever more effective methods of treatment which can provide a higher quality of life for longer periods.

It has now surprisingly been found that administration of a cortisol antagonist is effective in the treatment of heart failure and symptoms associated with heart failure.

Thus, in one aspect, the present invention provides the use of a cortisol antagonist for the manufacture of a medicament for the treatment of heart failure.

'Heart failure' can be defined clinically as a syndrome of ventricular dysfunction accompanied by reduced exercise capacity. Typically, there is a characteristic pattern of hemodynamic, renal and neural responses. In effect, heart failure is the inability of the heart to pump blood at an adequate rate to fulfill tissue metabolic requirements or the ability to do so only at an elevated filling pressure. Heart failure typically results in an inability to drain away body fluid which may cause ascites (body fluid in abdominal cavity), this often being observed in backward heart failure and when the liver is swollen. Within this general definition, it is intended to include the following types of heart failure and cortisol antagonists are suitable for use in treating all of these:

Acute congestive heart failure, a rapidly occurring deficiency in cardiac output marked by venocapillary congestion, hypertension and oedema, usually pulmonary oedema.

Backward heart failure, a concept of heart failure stating that imbalance of performance of the ventricles due to dysfunction of one results in a rise in pressure behind that ventricle, with backward transmission of the increased pressure and consequent rise in venous pressure and distension.

Congestive heart failure (CHF), a clinical syndrome due to heart disease, characterised by breathlessness and abnormal sodium and water retention, often resulting in oedema. The congestion may occur in the lungs or peripheral circulation or both, depending on whether the heart failure is right-sided or general.

Diastolic heart failure, heart failure due to a defect in ventricular filling caused by an abnormality in diastolic function.

Forward heart failure, a concept of heart failure that emphasizes the inadequacy of cardiac output relative to body needs; oedema is attributed primarily to renal retention of sodium and water, and venous distension is considered a secondary feature.

High-output heart failure, heart failure in which the cardiac output remains high enough to maintain a brisk circulation with warm extremities but is inadequate to meet demand; it is most often associated with hyperthyroidism, anemia, arteriovenous fistulas, beriberi, osteitis deformans or sepsis.

Left-sided heart failure, left ventricular failure, failure of adequate output by the left ventricle despite an increase in distending pressure and in end-diastolic volume, with dyspnea, orthopnea and other signs and symptoms of pulmonary congestion and oedema.

Low-output heart failure, heart failure in which cardiac output is decreased, as in most forms of heart disease, leading to clinical manifestations of impaired peripheral circulation and peripheral vasoconstriction (cold, pale extremities, cyanosis, narrowed pulse pressure).

Right-sided heart failure, right ventricular failure, failure of proper functioning of the right ventricle, with venous engorgement, hepatic enlargement, and subcutaneous oedema; it is often combined with left-sided heart failure.

Systolic heart failure, heart failure due to a defect in expulsion of blood caused by an abnormality in systolic function.

A cortisol antagonist is particularly well suited to the treatment of congestive, diastolic, backward, low-output and right-sided heart failure. Thus, the treatment of these conditions represents a preferred aspect of the present invention.

According to the New York Functional Classifications (Ganiats, T. G., Browner, D. K., Dittrich, H. C. in American Heart Journal (1998) 135: 5 Pt 1, 819–824) the severity of heart failure can be divided into four classes as follows:

Class I—no limitation of physical activity: ordinary physical activity does not cause undue fatigue, shortness of breath or palpitation;

Class II—slight limitation of physical activity; such patients are comfortable at rest, ordinary physical activity results in fatigue, shortness of breath, palpitations or angina;

Class III—marked limitation of physical activity; although patients are comfortable at rest, less than ordinary activity will lead to symptoms;

Class IV—inability to carry out any physical activity without discomfort: symptoms of congestive heart failure are present even at rest. With any physical activity increased discomfort is experienced.

Cortisol antagonists are suitable for the treatment of all classes of heart failure, particularly classes II to IV.

By 'cortisol antagonist' is meant any compound or agent which reduces production of cortisol or circulating levels of biologically active cortisol or which limits the biological effects of cortisol by inhibiting cortisol (glucocorticoid) receptors competitively or non-competitively, or in any other way. The term includes agents which interfere with the regulation of cortisol synthesis along the so-called hypothalmic-pituitary-adrenal gland (HRA) axis. Thus a "cortisol antagonist" may broadly be regarded as any compound or agent which antagonises or inhibits (i.e. reduces or prevents) cortisol activity.

A large number of agents are known to suppress glucocorticoid production or inhibit their receptor binding in humans: sodium valporate (Aggernaes, H. et al. Acta Psychiatr. Scand. (1988) 77 170–174); Enkephalins and their synthetic analogues (Stubbs, W. A. et al. The Lancet (1978) 1225–1227); Opioids such as loperamide, commercially available under the trademark IMODIUM from Janssen Pharmaceutica N.V.; the antihypertensive drug Clonidine (Slowinska-Srzednicka, J. et al. European Journal of Clinical Pharmacology (1988) 35 115–121); Oxytocin (Legros, J. J. et al. Endocrinologica (1987) 114 345–349) and Mifepristone, known as RU 486 or RU 38486 available from Roussel-Uclaf. Mifepristone and other antagonists which operate at the receptor level are a class of preferred active agents for use in the present invention.

Any of the above agents or any of the large number of cortisol synthesis inhibitors known in the art, e.g. econazole (Squibb, U.K.), ketoconazole and miconazole (Janssen, Belgium) and their derivatives, may be used as cortisol antagonists according to the present invention. In the case of econazole and miconazole, derivatives of these particular compounds are preferred.

'Derivatives' encompass compounds which are structurally related to the primary compound (e.g. ketoconazole) but are functionally equivalent or superior. Thus, a derivative might have a slightly inferior therapeutic activity but be a useful molecule because it exhibits reduced toxicity, is more convenient to formulate or administer etc. Derivatives may include salts or other variants which have been more significantly modified while retaining functionally important structural motifs in common with the primary compound. In the case of econazole and miconazole, such derivatives may exhibit better overall properties than the primary compounds in terms of therapeutic activity and toxicity, for example.

Preferred cortisol antagonists include those compounds which inhibit the synthesis of cortisol, either by reducing the production of cortisol in any form or which cause the production of a modified form of cortisol which is less biologically active than native, naturally occurring cortisol. Preferably, cortisol synthesis inhibitors will act on the cortisol synthetic pathway in a way which does not significantly affect the normal production of the other steroid hormones, in particular which does not significantly effect production of mineralocorticoids such as aldosterone. The 'significance' of the effect is considered in terms of the biological, in vivo, effect. Ketoconazole and its derivatives are preferred for use according to the invention and in addition, isomers of ketoconazole are known and may be used, individually or in combination (Rotstein et al., J. Med. Chem. (1992) 35, 2818–2825). The Cis-2S,4R and Cis-2R,4S isomers are particularly preferred for use in accordance with the present invention. These isomers may be used individually or in combination as in the commercially available product Fungoral™ (Janssen-Cilag, Belgium).

In the case of cortisol antagonists which act via cortisol (glucocorticoid) receptors, the antagonist will preferably have an effect on the receptors in the kidney and/or the heart. The binding affinity which an antagonist has for receptors in different organs may not be uniform and preferably the antagonist used in the present invention will have a comparatively higher binding affinity for the glucocorticoid receptors in the heart and/or kidney.

The cortisol antagonists for use according to the present invention have a sufficiently negative effect on circulating levels of biologically active cortisol or on its biological efficacy to cause a measurable and significant improvement in heart failure or its associated symptoms. It is not expected that in all cases treatment will be totally successful but "treatment" according to the present invention should include improvement in one or more of the following areas: fluid retention including oedema of lower limbs and fluid in the lungs (pulmonary oedema), dyspnea, liver enlargement, heart rate, stroke volume, shortness of breath, exercise intolerance and general physical and mental health. Particularly, improvements are seen in symptoms associated with fluid retention (e.g. liver enlargement, peripheral and pulmonary odema and ascites).

Advantageously, according to the uses and method of the present invention, one or more of the following benefits may be achieved:

a 10% or more reduction in liver size, a 10% or more reduction in heart rate, a 15% or more improvement in physical health according to the test described in the Examples herein.

Further symptoms which often occur with heart failure, whatever the cause, are enlargement of the heart and development of a fibrosis in the heart muscle. These morphological aspects of heart failure can also be treated successfully by administration of a cortisol antagonist.

Heart failure will be diagnosed when a patient has impaired cardiac function and exercise intolerance. All patients with heart failure, whether newly diagnosed or at a more advanced stage can be considered for treatment in accordance with the present invention. Treatment with a cortisol antagonist may be successful whatever the underlying disease which has resulted in a diagnosis of heart failure. The observations which have resulted in the present invention relate to the treatment of heart failure itself and its symptoms not to the diseases and risk factors which may give rise to heart failure. Various medical conditions such as cardiovascular disease may or may not lead to heart failure but as the implications for untreated heart failure are serious, it is beneficial to have available treatments specifically for heart failure and its associated symptoms.

Thus, in a further aspect is provided a method of treating heart failure in a mammal which method comprises administering a pharmaceutically effective amount of a cortisol antagonist to said mammal.

Alternatively viewed, according to the method of the invention, an amount of cortisol antagonist is administered which is effective to improve one or more of the symptoms of heart failure; these areas in which improvement may be observed are discussed above.

A 'pharmaceutically effective' amount can be determined with reference to the various areas discussed herein in which treatment may provide measurable improvements, and selected with reference to the Examples and standard practices for deciding dosage amounts.

Generally, patients in need of such a treatment will be diagnosed as suffering from heart failure by reference to the clinical definitions provided herein or other medically accepted criteria.

The cortisol antagonist or antagonists may be administered to the patient in any convenient form, orally or by intravenous, enteral or parenteral routes. Preferably the cortisol antagonist will be administered by oral routes.

Alternatively viewed, the invention provides a method of improving cardiac function and reducing exercise intolerance in a mammal which method comprises administering a pharmaceutically effective amount of a cortisol antagonist to said mammal.

Likewise, the invention provides the use of a cortisol antagonist in the production of a medicament for improving cardiac function and reducing exercise intolerance.

An improvement in cardiac function may include a reduction in heart rate and/or an increase in stroke volume. Exercise intolerance is generally characterised by breathlessness and other signs of fatigue, cramp etc., primarily due to an inability of the patient suffering from heart failure to supply sufficient oxygenated blood to muscle and other organs and tissue. It can be measured by a subnormal physical exercise test (Faggiano, P., D'Aloia, A., Gualeni, A. and Giordano, A. American Journal of Cardiology (1998) 15 81:4, 437–42).

Compositions comprising a cortisol antagonist as defined above are preferably formulated prior to administration.

The present invention therefore also provides a pharmaceutical composition for use in the treatment of heart failure, said composition comprising a cortisol antagonist together with at least one pharmaceutically acceptable carrier, diluent or excipient. The active ingredient in such compositions may comprise from 0.05% to 99% by weight of the formulation, more preferably 0.1% to 1.0%.

By "pharmaceutically acceptable" is meant that the ingredients must be compatible with other ingredients of the composition as well as physiologically acceptable to the recipient.

The pharmaceutical compositions may be formulated according to any of the conventional methods known in the art and widely described in the literature. Thus, the active ingredient may be incorporated, optionally together with other active substances, with one or more conventional carriers, diluents and/or excipients, to produce conventional galenic preparations such as tablets, pills, powders, lozenges, sachets, cachets, elixirs, suspensions, emulsions, solutions, syrups, aerosols (as a solid or in a liquid medium), ointments, soft and hard gelatin capsules, suppositories, sterile injectable solutions sterile packaged powders, and the like.

Examples of suitable carriers, excipients, and diluents are lactose, dextrose, sucrose, sorbitol, mannitol, starches, gum acacia, calcium phosphate, aglinates, tragacanth, gelatin, calcium silicate, microcrystalline cellulose, polyvinylpyrrolidone, cellulose, water syrup, water, water/ethanol, water/glycol, water/polyethylene, glycol, propylene glycol, methyl cellulose, methylhydroxybenzoates, propyl hydroxybenzoates, talc, magnesium stearate, mineral oil or fatty substances such as hard fat or suitable mixtures thereof. The compositions may additionally include lubricating agents, wetting agents, emulsifying agents, suspending agents, preserving agents, sweetening agents, flavouring agents, and the like. The compositions of the invention may be formulated so as to provide quick, sustained or delayed release of the active ingredient after administration to the patient by employing procedures well known in the art. Sustained and/or delayed release formulations may be particularly convenient.

The active agents are preferably formulated into tablets, each tablet containing a predetermined amount of active ingredient.

Suitable doses will vary from patient to patient and can be determined by the physician in accordance with the weight, age and sex of the patient and the severity of the condition and also the particular antagonist selected. A typical total daily dose will be in the region of 50 or 100–1200 mg of a cortisol antagonist which may be administered as a single dose or in several smaller doses during the day. Typical single doses will be in the region of 100–800 mg. Administration may advantageously be at around 10.00 p.m. in order to reduce cortisol activity during the night when natural cortisol levels are at their highest. Ketoconazole is preferably administered as a daily dose of 200–1000 mg, e.g. 300–600 mg.

During the majority of the treatment period, typically 75% or more, effective treatment will be daily. By 'effective treatment' is meant that the circulating levels of the cortisol antagonist are at physiologically effective levels; this may be achieved by daily administration or, for example, by use of a controlled-released formulation which offers sustained release over several days or more.

Improvements in patients treated in accordance with the present invention may be seen immediately or after some (e.g. 2–4) weeks and treatment should normally be continued for 3 months or more to achieve maximum benefits. As with most treatments for heart failure, it may be necessary to administer the cortisol antagonist for the rest of the patient's life. Such long term treatment may not necessarily be continuous and the optimum dose may vary during the course of treatment.

Use of a cortisol antagonist may be in place of or in addition to use of other drugs for the treatment of heart failure. This may improve the efficacy of the overall treatment regime and/or reduce the amount of drugs required by the patient or enable the physician to cease administration of a drug which is causing undesirable side effects.

As well as treatments which comprise the coadministration of a cortisol antagonist and one or more other drugs for the treatment of heart failure, medicaments and treatments in accordance with the present invention may comprise more than one cortisol antagonist. Treatment may involve administration of an antagonist which affects synthesis of cortisol in the adrenal glands and also treatment with an antagonist which inhibits the activity of cortisol at the receptor level. Furthermore treatment may involve administration of an antagonist which operates along the HPA axis as mentioned above.

Thus, in a further aspect the present invention provides a product containing (a) a cortisol antagonist and (b) a second drug (e.g. a second agent effective in the treatment of heart failure) as a combined preparation for simultaneous, separate or sequential use in the treatment of heart failure or in improving cardiac function and reducing exercise intolerance.

Suitable 'second drugs or agents' include known drugs for use in the treatment of heart failure as are discussed above e.g. diuretics, vasodilators, inotropic drugs, ACE inhibitors and angiotensin II antagonists and also a second cortisol antagonist as defined herein.

Where two or more active agents are administered, they may be given simultaneously to the patient or times of administration may be staggered throughout the day or treatment cycle.

The invention will be further described with reference to the following non-limiting Examples.

EXAMPLE 1

Subject 1: A 44 year old man exhibiting the symptoms of heart failure, including retention of body fluid manifested as moderate oedema of lower limbs and body fluid in the lungs. Also, moderate dyspnea and increased heart rate as well as an increase in liver size (indicative of fluid retention in the liver). Patient being treated for heart failure with lisinopril (Zestril®)

Treatment: 400 mg of a racemate of the Cis-2S,4R and Cis-2R,4S isomers of ketoconazole (Fungoral™ tablets—Janssen-Cilag, Belgium) was administered at 10.00 pm every day for a 3 month period.

Observations: Body weight reduced by 3.8 kg—attributable to a reduction in fluid retention.
Heart rate fell from 72 beats/min to 62 beats/min.
Reduction in liver size of 10% and a resulting reduction in liver transaminases
S-ASAT reduced from 0.44 to 0.30 $\mu$Kat/L
S-ALAT reduced from 1.0 to 0.39 $\mu$Kat/L
Dyspnea, oedema of lower limbs and body fluid in the lungs reduced.
Physical health as measured by a subnormal physical exercise test (Faggiano, P. et al. supra) improved by 15%.
Dose of lisinopril (Zestril®) could be reduced to half of original dose

EXAMPLE 2

Subject 2: A 63 year old woman exhibiting the same symptoms of heart failure as subject 1. Patient being treated for heart failure with furosemid (40 mg/day)
Treatment: As for Example 1.
Observations: Body weight reduced by 4.2 kg.
Heart rate fell from 74 beats/min to 60 beats/min.
Reduction in liver size of 15% and in liver transaminases.
S-ASAT reduced from 0.58 to 0.32 $\mu$Kat/L
S-ALAT reduced from 0.92 to 0.68 $\mu$Kat/L
Dyspnea, oedema of lower limbs and body fluid in lungs reduced.
Physical health, as measured by a subnormal physical exercise test, improved by 20%.
Dose of furosemid could be stopped within 6 weeks of commencement of treatment with ketoconazole.

What is claimed is:

1. A method for the treatment of heart failure in a mammal which comprises administering a cortisol antagonist to said mammal in an amount effective to treat the heart failure, with the proviso that said cortisol antagonist is not clonidine.

2. The method of claim 1 wherein the heart failure is selected from the group consisting of congestive heart failure, diastolic heart failure, low-output heart failure, right-sided heart failure, cardiac hypertrophy, and cardiac fibrosis.

3. The method of claim 2 wherein the cortisol antagonist is an inhibitor of cortisol synthesis.

4. The method of claim 3 wherein the inhibitor of cortisol synthesis is ketoconazole or a derivative thereof.

5. The method of claim 4 wherein the cortisol synthesis inhibitor is a Cis-2S,4R and/or Cis-2R, 4S isomer of ketoconazole.

6. The method of claim 1, wherein the daily dose of cortisol antagonist being administered to the subject being treated is 100–1200 mg.

7. The method of claim 1, wherein the daily dose of cortisol antagonist being administered to the subject being treated is 100–800 mg.

8. The method of claim 1, wherein the cortisol antagonist is ketoconazole and the daily dose of ketoconazole being administered to the subject being treated is 300–600 mg.

9. A method for the treatment of one or more symptoms associated with heart failure selected from the group comprising edema of lower limbs, pulmonary edema, dyspnea, liver enlargement, increased heart rate, reduced stroke volume, shortness of breath and exercise intolerance which comprises administering, in a daily dose, a cortisol antagonist to a mammalian subject, with the proviso that said cortisol antagonist is not clonidine.

10. The method of claim 9 wherein the symptom is pulmonary edema.

11. The method of claim 9 wherein the daily dose of the cortisol antagonist administered to the subject being treated is 100–1,200 mg.

12. The method of claim 9 wherein the daily dose of the cortisol antagonist administered to the subject being treated is 100–800 mg.

13. The method of claim 9 wherein the cortisol antagonist is ketoconazole and the daily dose of ketoconazole being administered to the subject being treated is 300–600 mg.

* * * * *